US 6,652,696 B2

(12) United States Patent
Kuen et al.

(10) Patent No.: US 6,652,696 B2
(45) Date of Patent: Nov. 25, 2003

(54) CROSS DIRECTION METHOD FOR MAKING A REFASTENABLE GARMENT WITH OVERLAID SIDE PANELS

(75) Inventors: David Arthur Kuen, Neenah, WI (US); Robert Lee Popp, Hortonville, WI (US); Joseph Daniel Coenen, Neenah, WI (US); Shawn A. Quereshi, Neenah, WI (US); Jack L. Couillard, Menasha, WI (US); Christopher Peter Olson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 121 days.

(21) Appl. No.: 09/815,789

(22) Filed: Mar. 23, 2001

(65) Prior Publication Data
US 2002/0138063 A1 Sep. 26, 2002

(51) Int. Cl.⁷ ................................. A61F 13/15
(52) U.S. Cl. .................. 156/204; 156/226; 156/269; 156/291
(58) Field of Search .................. 156/66, 199, 204, 156/226, 227, 269, 291; 604/385.21, 385.29, 391

(56) References Cited

U.S. PATENT DOCUMENTS

| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,145,763 A | 3/1979 | Abrams et al. |
| 4,205,679 A | 6/1980 | Repke et al. |
| 4,340,563 A | 7/1982 | Appel et al. |
| 4,402,690 A | 9/1983 | Redfern |
| 4,610,680 A | 9/1986 | LaFleur |
| 4,615,695 A | 10/1986 | Cooper |
| 4,663,220 A | 5/1987 | Wisneski et al. |
| 4,699,622 A | 10/1987 | Toussant et al. |
| 4,704,116 A | 11/1987 | Enloe |
| 4,940,464 A | 7/1990 | Van Gompel et al. |
| 5,046,272 A | 9/1991 | Vogt et al. |
| 5,087,253 A | 2/1992 | Cooper |
| 5,104,116 A | 4/1992 | Pohjola |
| 5,224,405 A | 7/1993 | Pohjola |
| 5,226,992 A | 7/1993 | Morman |
| 5,370,634 A | 12/1994 | Ando et al. |

(List continued on next page.)

FOREIGN PATENT DOCUMENTS

| EP | 0 217 032 | 4/1987 | |
| EP | 0 650 714 A1 | 5/1995 | ........... A61F/13/15 |
| EP | 757 550 | 12/1998 | |
| EP | 0755238 B1 | * 8/1999 | |
| GB | 1 520 740 | 8/1978 | |
| WO | WO 84/04242 | 11/1984 | ........... A61F/13/16 |
| WO | 95/27462 | 10/1995 | |
| WO | WO 97/46197 | * 12/1997 | |
| WO | 00/23025 | 4/2000 | |
| WO | 00/35395 | 6/2000 | |
| WO | 00/35398 | 6/2000 | |
| WO | 00/37009 | 6/2000 | |

*Primary Examiner*—Adrienne C. Johnstone
*Assistant Examiner*—Barbara J. Musser
(74) *Attorney, Agent, or Firm*—Pauley Petersen & Erickson

(57) ABSTRACT

A prefastened absorbent garment is manufactured with its longitudinal axis in the cross machine direction. A web of garment chassis material extending in the machine direction is overlaid within the garment chassis borders. The side panel webs are attached to the chassis web and have hook and loop fasteners thereon. The garment can be individuated from the combined chassis and side panel webs.

18 Claims, 6 Drawing Sheets

U.S. PATENT DOCUMENTS

| | | |
|---|---|---|
| 5,779,831 A | 7/1998 | Schmitz |
| 5,785,699 A | 7/1998 | Schmitz |
| 5,795,350 A | 8/1998 | Schmitz |
| 5,830,206 A | 11/1998 | Larsson |
| 5,855,574 A | 1/1999 | Kling et al. |
| 5,897,545 A | 4/1999 | Kline et al. |
| 6,287,287 B1 | 9/2001 | Elsberg |
| 6,328,725 B2 * | 12/2001 | Fernfors ............... 604/391 |
| 6,395,115 B1 | 5/2002 | Popp et al. |
| 6,409,858 B1 | 6/2002 | Popp et al. |
| 6,432,243 B1 | 8/2002 | Popp et al. |
| 6,432,248 B1 | 8/2002 | Popp et al. |
| 6,447,628 B1 | 9/2002 | Couillard et al. |
| 6,461,344 B1 * | 10/2002 | Widlund et al. ............ 604/390 |
| 6,481,362 B2 | 11/2002 | Hietpas et al. |
| 6,497,032 B2 | 12/2002 | Maxton et al. |
| 6,513,221 B2 | 2/2003 | Vogt et al. |
| 6,514,187 B2 | 2/2003 | Coenen et al. |
| 2002/0111596 A1 * | 8/2002 | Fletcher et al. ........ 604/385.03 |

* cited by examiner

US 6,652,696 B2

CROSS DIRECTION METHOD FOR MAKING A REFASTENABLE GARMENT WITH OVERLAID SIDE PANELS

BACKGROUND OF THE INVENTION

In the known art, there have been two ways of making a garment web into point of sale items. One is to put refastenable tabs, such as adhesive tape or hook and loop combinations onto the garment body, in the manner of an infant diaper, for later use to secure the back panel of the diaper to the front panel. A second is to bond the side edges of the front and back sections together to make a closed garment with fixed seams, in the manner of a training pant which is slid on and off the wearer like a regular adult garment. To remove such a garment if it becomes soiled, it is necessary to break the side region, i.e. tear the sides of the product from waist opening to leg hole, in order to remove the garment like a diaper, as convenience and hygiene would dictate.

It is therefore desired to provide a garment, such as a training pant, which may be slid-on in the fashion of adult underwear while being easily removeable in the manner of a diaper and which can be made with relatively uncomplicated machinery in a space-efficient manner.

SUMMARY OF THE INVENTION

The present invention can provide a readily and inexpensively producible refastenable incontinence garment. The garment can be desirably manufactured with its longitudinal axis in the cross machine, or cross, direction. A web of garment chassis materials extending in the machine direction can be overlaid with side panel webs. The side panel webs are attached to the chassis web at bonds spaced in the machine direction and have a first and a second cooperative fastener member, such as hook and loop fasteners, opposing each other in the cross direction. The side panels desirably do not extend beyond the chassis web, making the manufacturing process very compact. The manufactured garment is also compact and needs only one fold to place it in condition for packaging. The fold can place the cooperative fasteners in a fastening relationship. Each fastener member can be perforated, cut, or weakened at its midline such that the side panel webs will separate into left and right side panels upon opening the garment for use. The side panel webs are desirably shaped at selected edges to provide an efficacious leg hole fit. The side panel webs are further desirably elastic, extensible, or stretchable in the transverse direction of the resultant garment to provide an efficacious garment fit for the manufactured garment.

BRIEF DESCRIPTION OF THE DRAWINGS

These and other objects and features of this invention will be better understood from the following detailed description taken in conjunction with the drawings wherein.

DEFINITIONS

Figure 1:
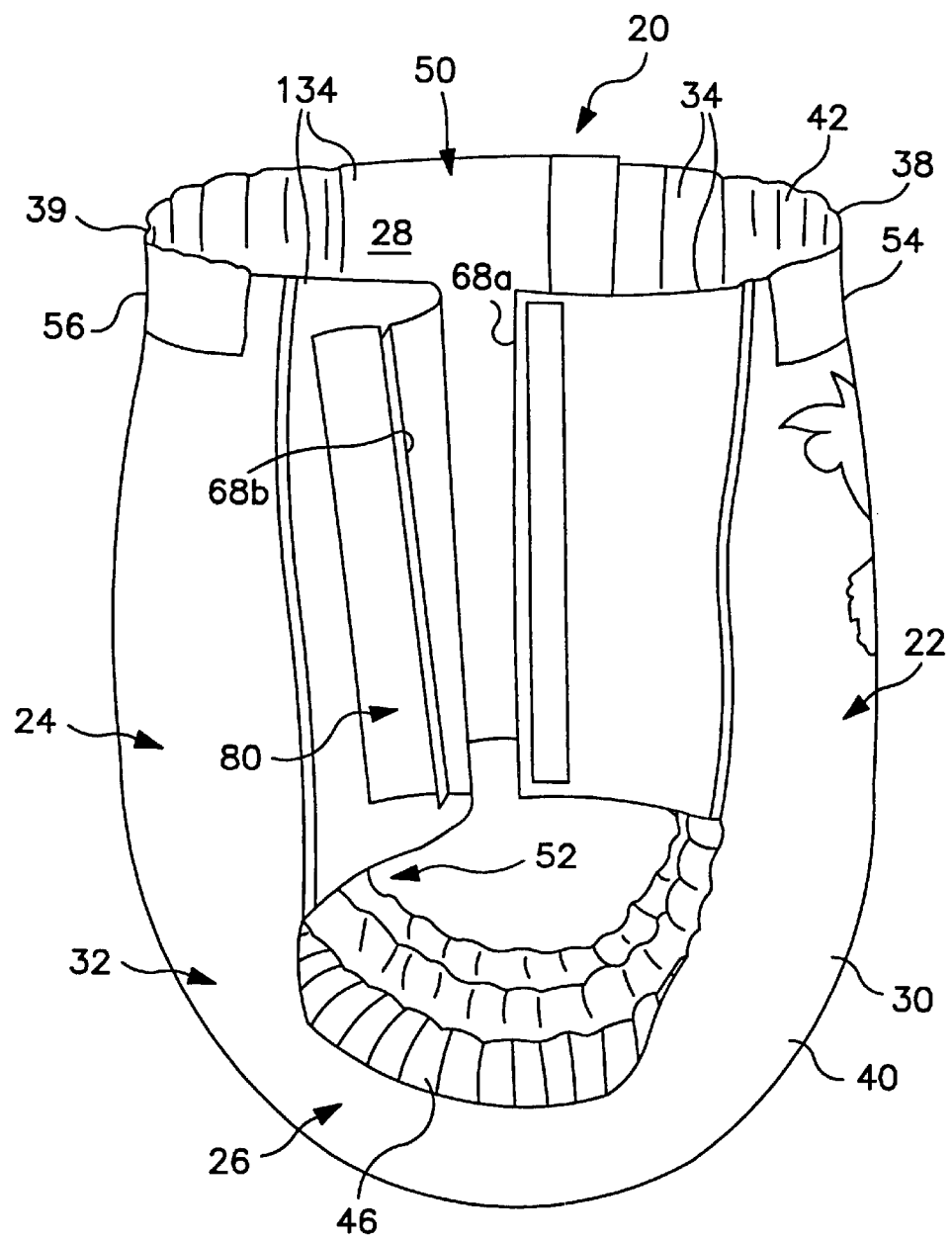
FIG. 1 is a side perspective view of an absorbent garment having refastenable side seams.

Within the context of this specification, each term or phrase below will include the following meaning or meanings.

"Article" refers to a garment or other end-use article of manufacture.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Chassis web" or "garment chassis web" for purposes of the present invention refers to that portion of an in-process or finished absorbent article or garment exclusive of any non-integral side panels. A chassis web may be nonabsorbent, or absorbent with, or without, having specially adapted absorbent structures added thereto.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation. "Extensible" implies stretchability without recovery of the original size or shape.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more desirably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Flexible" refers to materials which are compliant and which will readily conform to the general shape and contours of the wearer's body.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic. "Integral" or "integrally" is used to refer to various portions of a single unitary element rather than separate structures bonded to or placed with or placed near one another.

"Layer" when used in the singular can have the dual meaning of a single element or a plurality of elements.

"Line of Weakness" is used to refer to a perforation, thinned area, nonpermanent or weak bond, or other means for facilitating separation of a material, a fabric, or a layer of such material or fabric, whether defined by function or fabric type.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 3:
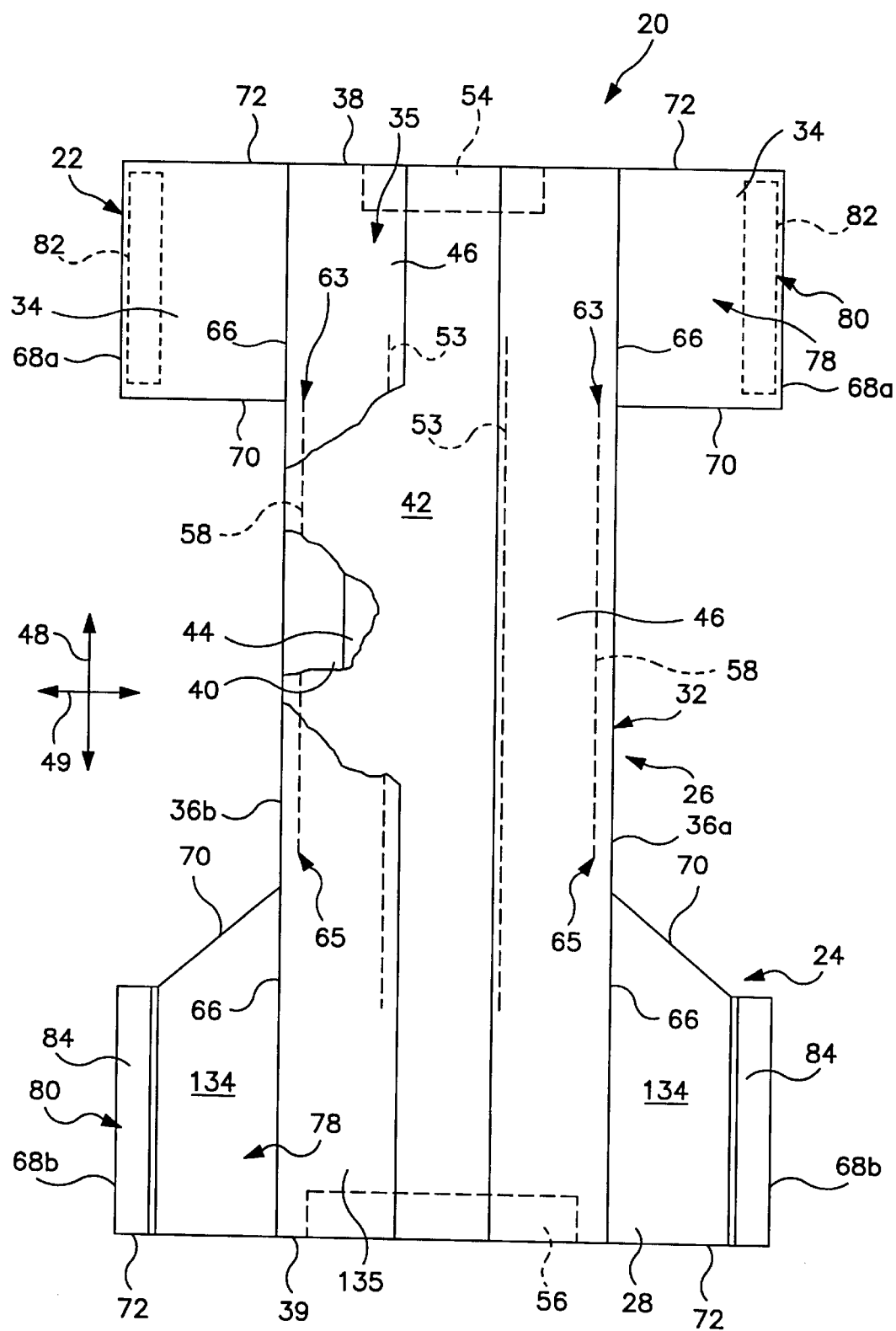
FIG. 3 is a plan view of an absorbent garment in a partially disassembled, stretched flat state, and showing the surface of the article that faces the wearer when the article is worn, and with portions cut away to show the underlying features.

"Longitudinal" and "transverse" have their customary meaning, as indicated by the longitudinal and transverse axes directions depicted in FIG. 3. The longitudinal axis of a garment, or absorbent article, lies in the plane of the article and is generally parallel to a vertical plane that bisects a standing wearer into left and right body halves, when the article is worn. The transverse axis lies in the plane of the article generally perpendicular to the longitudinal axis. The article, although illustrated as longer in the longitudinal direction than in the transverse direction, need not be so.

"Machine direction" refers to the direction in which the web travels, as opposed to "cross direction" or "cross machine direction" which refers to a direction generally perpendicular to the machine direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are desirably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

Words of degree, such as "Substantially", "About", and the like are used herein in the sense of "at, or nearly at, when given the manufacturing and material tolerances inherent in the stated circumstances" and are used to prevent the unscrupulous infringer from unfairly taking advantage of the invention disclosure where exact or absolute figures are stated as an aid to understanding the invention.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S.

Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PREFERRED EMBODIMENTS

The principles of the present invention can be incorporated into any suitable garment and especially disposable, or limited use garments. Examples of such suitable garments may include, but are not limited to, diapers, training pants, incontinence products, other personal care or health care garments, or the like. For ease of explanation, the description hereafter will be in terms of a child's training pant.

Figure 2:
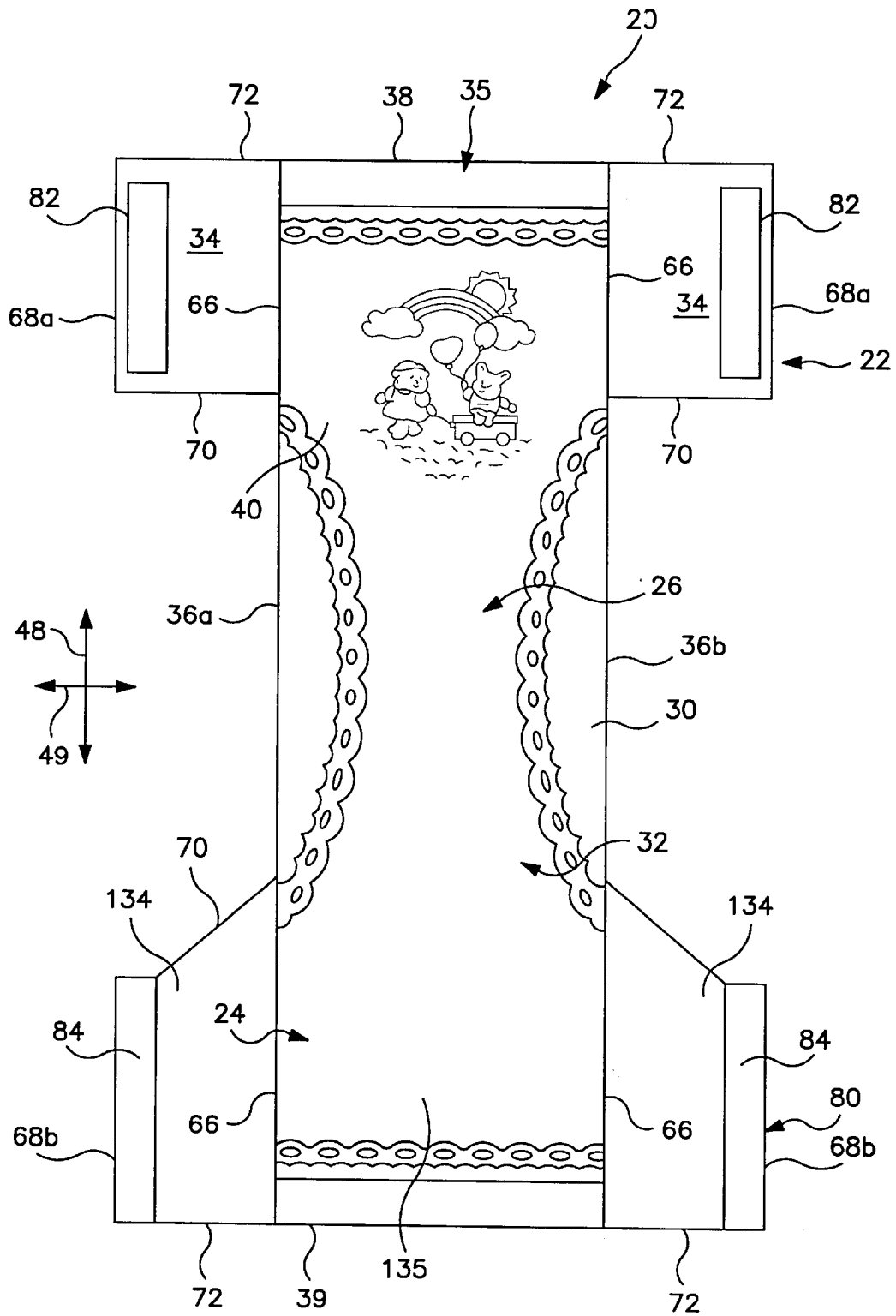
FIG. 2 is a plan view of an absorbent garment in a partially disassembled, stretched flat state, and showing the surface of the article that faces away from the wearer when the article is worn.

Referring to FIGS. 1–3, one such example is a disposable absorbent garment, such as a training pant 20, as illustrated for broad purposes of explanation of the environment of the present invention. The training pant 20 includes an absorbent chassis 32 and a fastening system 80. The absorbent chassis 32 helps define for the garment a front region 22, a back region 24, a crotch region 26 interconnecting the front and back regions, an inner surface 28 which is configured to contact the wearer, and an outer surface 30 opposite the inner surface which is configured to contact the wearer's clothing. The absorbent chassis 32 also defines a pair of transversely opposed side edges 36a, 36b and a pair of longitudinally opposed waist edges, which are designated front waist edge 38 and back waist edge 39. The front region 22 is contiguous with the front waist edge 38, and the back region 24 is contiguous with the back waist edge 39.

The illustrated absorbent chassis 32 may have a generally rectangular composite structure but may include other shapes such as those having leg cut outs, hour glass shapes or other suitable shapes. Attached to the absorbent chassis 32 are a pair of transversely opposed front side panels 34, and a pair of transversely opposed back side panels 134. The illustrated absorbent chassis 32 desirably includes an outer cover 40, a bodyside liner 42 which is connected to the outer cover in a superposed relation, an absorbent assembly 44 (FIG. 3) which is located between the outer cover 40 and the bodyside liner 42, and a pair of containment flaps 46 (FIG. 3). Although illustrated as having an absorbent assembly, the chassis structure of the present invention need not include any specially adapted absorbent structures. For reference, arrows 48 and 49 depicting the orientation of the longitudinal axis and the transverse axis directions, respectively, of the training pant 20 are illustrated in FIGS. 2 and 3.

With the training pant 20 in the partially fastened position as illustrated in FIG. 1, the side panels 34, 134 join front and back regions 22 and 24 including the front and back center panels 35, 135 together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 134 include the portions of the training pant 20 which, when worn, are positioned on the hips of the wearer.

The front region 22 of the training pant 20 includes the transversely opposed front side panels 34 and a front center panel 35 (FIGS. 2 and 3) positioned between and interconnecting the side panels 34, along with a front waist elastic member 54 and any other connected components. The back region 24 of the training pant 20 includes the transversely opposed back side panels 134 and a back center panel 135 (FIGS. 2 and 3) positioned between and interconnecting the side panels 134, as well as a rear waist elastic member 56 and any other connected components. The waist edges 38 and 39 of the absorbent chassis 32 and waist edges 72 of the side panels 34, 134 are configured to encircle the waist of the wearer when worn and provide the waist opening 50 which defines a waist perimeter dimension. Portions of the transversely opposed side edges 36a, 36b and leg edges 70 of the side panels 34, 134 in the crotch region 26 generally define the leg openings 52.

The training pant 20 is configured to contain and/or absorb any body exudates discharged from the wearer. For example, the absorbent chassis 32 desirably although not necessarily includes the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges 36a, 36b of the absorbent chassis 32, and can extend longitudinally along the entire length of the absorbent chassis 32 or may only extend partially along the length of the absorbent chassis 32. Suitable constructions and arrangements for the containment flaps 46 are generally well known to those skilled in the art and are described in U.S. Pat. No. 4,704,116 issued Nov. 3, 1987 to Enloe.

To further enhance containment and/or absorption of body exudates, the training pant 20 desirably includes the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the transversely opposed side edges 36a, 36b and positioned in the crotch region 26 of the training pant 20. The leg elastic members 58 are desirably longitudinally aligned along the transversely opposed side edges 36a, 36b. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E. I. DuPont de Nemours and Company, Wilmington, Del., U.S.A.

The outer cover 40 desirably includes a material that can be substantially liquid impermeable, and can be elastic, stretchable or nonstretchable. The outer cover 40 can be a single layer of liquid impermeable material, but desirably includes a multi-layered laminate structure in which at least one of the layers can be liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 can be made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer can be desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, can be a 0.2 millimeter polyethylene film commercially available from Huntsman Packaging of Newport News, Va., U.S.A. If the outer cover 40 can be a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material can be composed of a microporous polymer film or a nonwoven fabric that has been coated or otherwise treated to impart a desired level of liquid impermeability. A suitable microporous film can be a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Hodgson Textile Chemicals of Mount Holly, N.C., U.S.A. and GLUCOPON® 220UP from Henkel Corporation of Ambler, Pa., in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 can be a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly 44 (FIG. 3) can be positioned between the outer cover 40 and the bodyside liner 42, which components can be joined together by any suitable means, such as adhesives, as is well known in the art. The absorbent assembly 44 can be any structure which can be generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonunifornly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 can be generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material can be present in the absorbent assembly 44 in an amount of from about 0 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly.

The absorbent chassis 32, if desired, can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded to the absorbent chassis 32 in the respective front and back regions 22 and 24, and are releasably attached to one another by a fastening system 80 when the training pant is worn. More particularly, as shown best in FIGS. 2 and 3, the front side panels 34 can be permanently bonded to the transversely opposed side edges 36a, 36b in the front region 22 along attachment lines 66, and the back side panels 134 can be permanently bonded to the transversely opposed side edges 34a, 34b in the back region 24 along attachment lines 66. The side panels 34 and 134 may be attached using attachment means known to those skilled in the art such as adhesive, thermal or ultrasonic bonding, or a combination thereof.

In particular embodiments for improved fit and appearance, the side panels 34 and 134 desirably have an average length dimension measured parallel to the longitudinal axis direction 48 that can be about 20 percent or greater, and particularly about 25 percent or greater, of the overall length dimension of the absorbent article, also measured parallel to the longitudinal axis. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 in particular may have a continually decreasing length dimension moving from the attachment line 66 to a distal edge 68b of the back panel 134, as shown in FIGS. 2 and 3.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material. Still alternatively, each individual side panel 34 and 134 can include a single piece of material which is folded over upon itself along an intermediate fold line (not shown).

The side panels 34 and 134 desirably include an elastic material capable of stretching in a direction generally parallel to the transverse axis direction 49 of the training pant 20. In particular embodiments, the front and back side panels 34 and 134 may each include an interior portion 78 disposed between the distal edge 68a, 68b and the respective front or back center panel 35 or 135. In the illustrated embodiment in FIG. 3, the interior portions 78 are disposed between the distal edges 68a, 68b and the transversely opposed side edges 36a, 36b of the absorbent chassis 32. The elastic material of the side panels 34 and 134 can be disposed in the interior portions 78 to render the side panels elastomeric in a direction generally parallel to the transverse axis. Most desirably, each side panel 34 and 134 can be elastomeric from a waist end edge 72 to a leg end edge 70. More specifically, individual samples of side panel material, taken between the waist end edge 72 and the leg end edge 70 parallel to the transverse axis direction 49 and having a length from the attachment line 66 to the distal edge 68a, 68b and a width of about 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al. Alternatively, the side panel material may include other woven or nonwoven materials, such as those described above as being suitable for the outer cover 40 or bodyside liner 42, or stretchable but inelastic materials.

The training pant 20 according to the present invention also includes a fastening system 80 for securing the training pant about the waist of the wearer (FIG. 1). The illustrated fastening system 80 includes fastening components 82 that are adapted to refastenably connect to mating fastening components 84. In one embodiment, one surface of each of the fastening components 82 and 84 includes a plurality of engaging elements that project from that surface. The engaging elements of the fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. The fastening components 82 and the mating fastening components 84 are desirably rectangular, although they may alternatively be square, round, oval, curved or otherwise non-rectangularly shaped and may comprise a plurality of individual fastening elements or an entire surface of a side panel if so desired.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 or the mating fastening components 84 are available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a unidirectional hook pattern and having a thickness of about 0.051 millimeters (2 mils).

Figure 4:
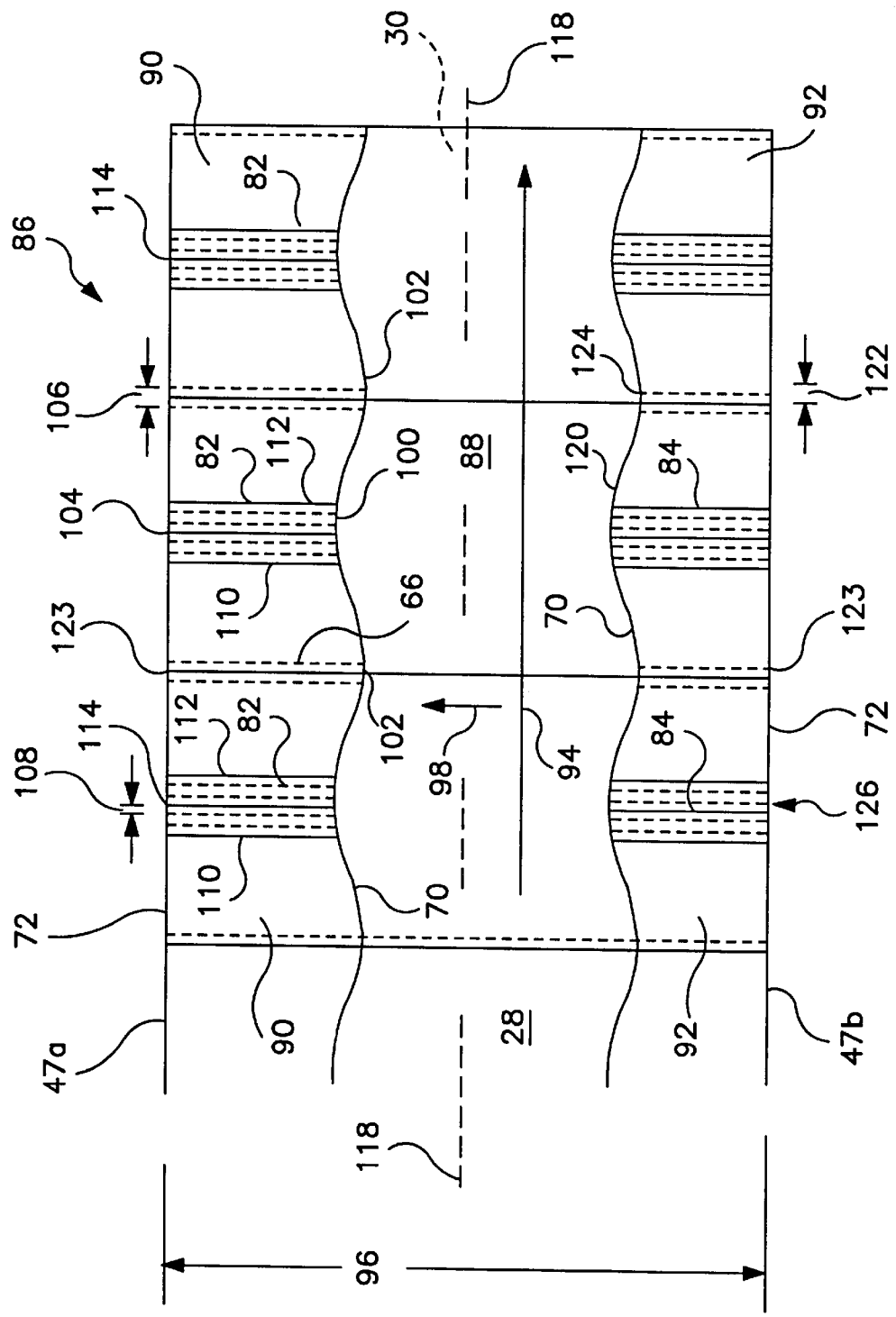
FIG. 4 shows an in-process manufacture of the absorbent garment with refastenable side seams according to one embodiment of the present invention.

Referencing FIG. 4, a refastenable garment web 86 can be made from a garment chassis web 88 and first and second side panel webs 90 and 92 respectively. The chassis web 88 can be desirably absorbent and may be suitably constructed with any necessary materials, layers, or components discussed above or as known in the art to produce the desired functionality of an incontinence garment or the like. The chassis web 88 includes the inside, or liner or interior, surface 28 to be placed against the skin of the wearer, and the outside or exterior surface 30. As is known, the chassis web 88 is transported for manufacture with its longitudinal axis in, or defining, the machine direction 94 and having a width 96 transverse thereto in the cross machine, or cross, direction 98 between first and second garment web width edges 47a, 47b respectively.

The first side panel web 90, comprising any suitable material as known in the art, e.g., spunbond laminate, desirably with elasticity, or extensibility, in the machine direction 94 so as to extend in the transverse direction of the resultant garment; is laid over the interior surface 28 of the chassis web 88 and attached thereto, although attachment to the exterior surface 30 may be done. The first side panel web 90 has a first, straight, waist edge 72 and, in the illustrative embodiment, a second, shaped, leg opening edge 70, here shown as sinusoidal although other shapes including straight, are possible. The first side panel web 90 waist edge 72 is aligned with the first width edge 47a of the chassis web 88.

In the exemplary embodiment, first fastener strips, collectively 82 are bonded to the first side panel web 90 at regular intervals along the machine direction. The first fastener strips 82 are represented as the loop portion of a cooperative hook and loop mechanical fastener system although other suitable fastening systems may be used. The first fastener strips 82, which may also be the hook half of the fastener system if desired, extend, desirably, but not necessarily, the entire width of the first side panel web, i.e. from waist end edge 72 to leg end edge 70 in the cross direction. The second, sinusoidal, leg opening edge 70 of course has varying widths between the waist edge 72 with troughs 100 in the sinusoidal edge being closer to the first straight waist edge 72 and crests 102 being farthest therefrom. The longitudinal axis or midline 104, of the first fastener strip 82 is centered at the troughs 100 to allow the crests 102 to provide a sufficient back portion of the garment side panel for coverage of the buttock area of the wearer as will be appreciated upon a thorough understanding of the present invention.

The first side panel web 90, desirably with the fastener strip previously disposed thereon, can be connected, desirably in an ultrasonic bond with adhesive reinforcement at attachment lines 66 to the chassis web 28. Attachment lines 66 for the first side panel web 90 occur at each crest point 102 if the leg opening edge 70 is sinusoidal. The bond is of a selected width 106.

Figure 5:
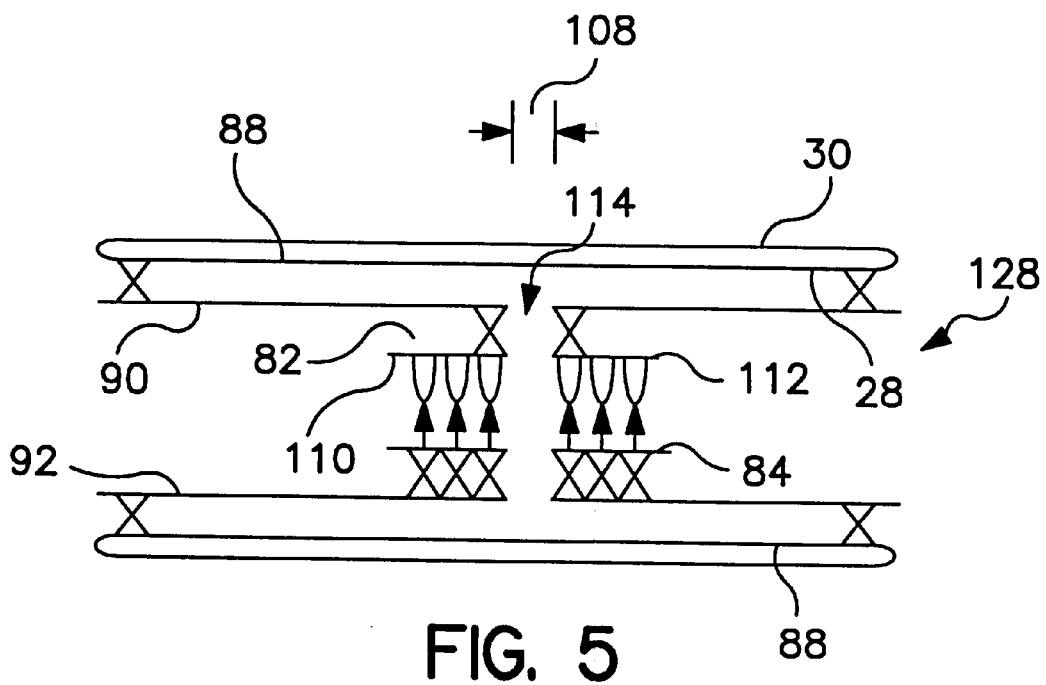
FIG. 5 shows a top, or end, view as seen at the waistband area of a folded absorbent garment according to an embodiment of the present invention.
Figure 6:
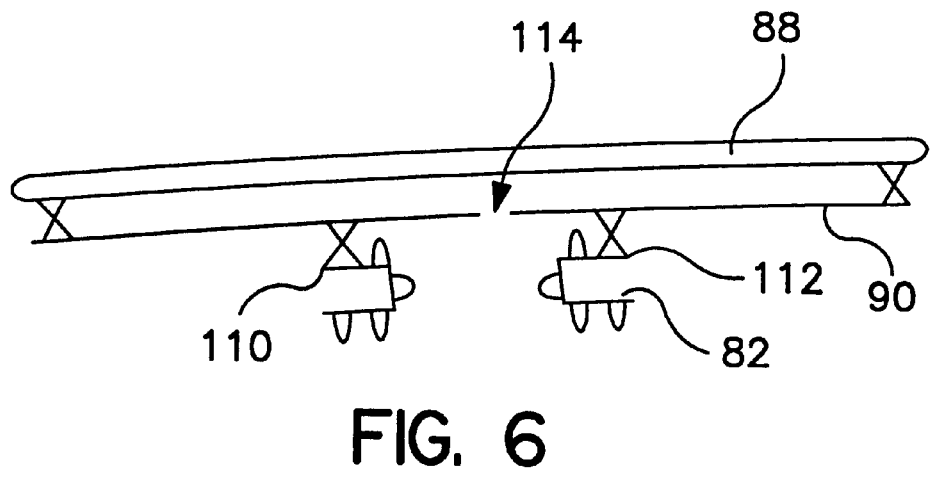
FIG. 6 illustrates the bonding and perforation of one fastening means and side panel web of the garment according to alternate embodiments of the present invention.
Figure 7:
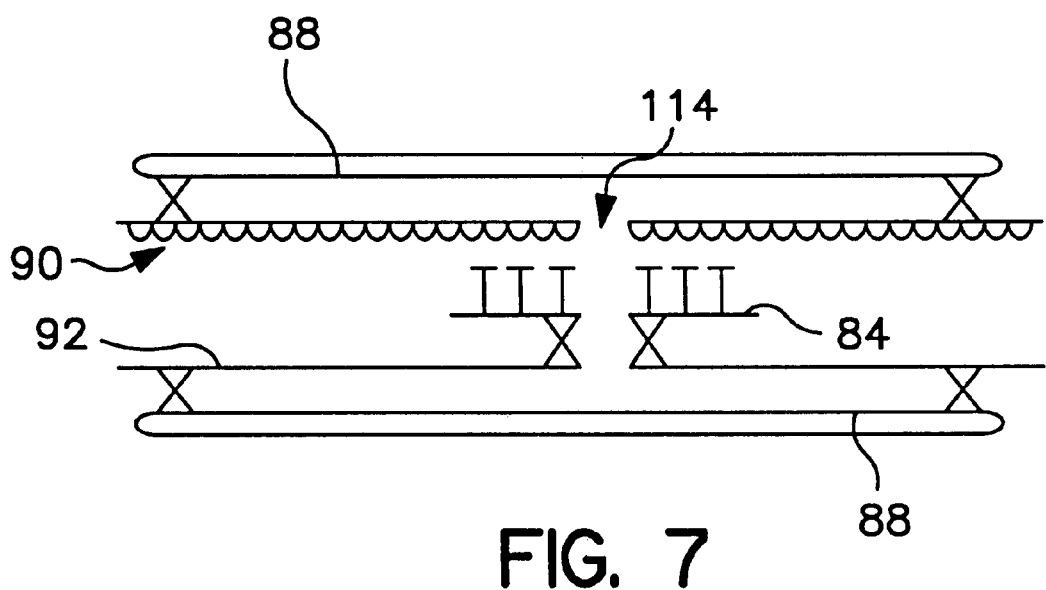
FIG. 7 illustrates an end view at the waistband area of a garment having a panel with one fastener component disposed on the entire surface thereof.

The first, or loop, fastener strip 82, if a separate member, can be adhered, or bonded, desirably ultrasonically, or otherwise secured to the first side panel web 90 along the fastener midline 104 with a bond of a specified width 108 and left free at its peripheral edges 110, 112 to create a hinged attachment as seen in FIG. 5. The loops face up, or out of the plane of the paper in FIG. 4, and away from the first side panel 90. The width of the bond 108 can be then bisected by a perforation line 114, desirably at the fastener midline 104, and extending through the thickness of the loop fastener and the underlying side panel material (see also FIGS. 5 and 6). The perforation line may be any form of cut or cuts necessary to achieve the separability of the side panel into later halves for use by the wearer while maintaining manufacturability of the garment. As an exemplary alternative, referencing FIG. 6, the fastener strip 82 may be bonded on the peripheral edges 110, 112 of its longitudinal direction with the exposed loop material facing the side panel web 90 and then perforated as before and folded to place the exposed loop material facing outwardly from the side panel web 90 material as shown. In another alternative, the first side panel web 90 may be made as a material layer which will function as a loop fastener without need for the addition of separate loop fastener strips. In this embodiment it is desirable to hingedly attach the hook fastening component 82 to its side panel web 92 as seen in FIG. 7. Bonds are indicated by "x"s in FIGS. 5–7.

The second side panel web 92, comprising any suitable material including, e.g., a spunbond laminate like the first side panel web 90, is laid over the interior surface 28 of the chassis web 88. The second side panel web 92 has a first, desirably straight, waist edge 72 and, as shown but not required, a shaped, or sinusoidal, second, leg opening edge 70. The second side panel waist edge 72 can be aligned with the chassis web second width edge 47b. The second side panel web leg opening shaped edge 70 is shown as a complementary sine curve whose crests 120 align with the first side panel web shaped edge troughs 100 across the chassis web midline 118. The first and second side panel webs 90, 92 can be cut from a single sheet of material along a single line of weakness or cut line that forms shaped leg edges 70. The first and second side panel webs may then be applied as a single web member if desired.

The second side panel web 92 can be then ultrasonically bonded and adhesively reinforced, or otherwise secured, in a selected width 122 to the chassis web 88 at each trough point 124 on the second side panel leg opening edge 70, desirably with the fastener strips already in place.

Second, hook, fastener elements 84 are secured, if need be, by ultrasonic bonding and adhesives, or the like, to the second side panel web 92 at its crest point 120 intervals, i.e. spaced along the machine direction, so as to be placed opposite the corresponding loop strips 82. The hook strips are desirably fully bonded to the panel over their entire surface in the illustrated embodiment. The hook fastener strip 84 and second side panel web 92 are likewise through cut or provided with a line of weakness along the longitudinal midline 126 of each second fastener strip.

The chassis web 88 can then be folded on its midline 118 to place the hook and loop fasteners in fastening opposition as shown in FIG. 5. The individuated garment 128 shown in FIG. 5 may be separated from the garment web 86 by a single cut at line 123 along the cross direction bisecting each of the aligned side panel bonds, either before or after the single fold of the chassis web which places the fasteners in fastening contact. If desired, the end user may be supplied with the garments unseparated, or separated but not folded.

Figure 8:
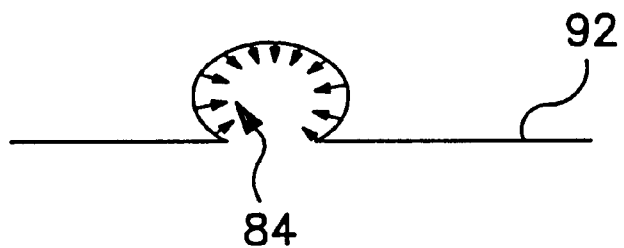
FIG. 8 shows a schematic end view of a folded side panel web which may be used with the present invention.

Referencing FIG. 8, a side panel web, e.g. 92, in some embodiments may comprise variously folded material, with or without fastener elements, e.g. 84, thereon in order to provide additional length to the side panels of the resultant garments within the scope of the present invention.

In general it will occur to the person of skill in the art that various constructions and arrangements of materials will be suitable for accomplishing the present invention as taught and claimed herein, including various foldings or placements of side panels, as made from first side panel web 90 or second side panel web 92, or both; and further including various placements and constructions of the fastening components 82, 84 relative to the side panels or their webs. For example, in an alternative embodiment not illustrated, the opposition of the fastening components could be provided by a folding of the side panels to take the fastening components from a position proximal the longitudinal axis of the garment and facing the interior surface of the chassis web, to a position proximal the transversely opposed side edges of the garment and facing away from the interior surface.

It will be appreciated that while the present invention has been described in terms of a single chassis web track traveling in the machine direction, efficiencies may be gained by practicing the teachings of the present invention in conjunction with multiple side-by-side tracks of chassis webs traveling in the machine direction.

While in the foregoing specification a compact, easily manufacturable, and desirably absorbent garment with refastenable side seams, and a method of making such a garment, has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method of making a refastenable garment with attached side panels and a longitudinal axis in the cross machine direction, comprising:
   a. providing a first side panel web with a waist edge and a leg opening edge;
   b. providing a garment chassis web with a longitudinal axis in the machine direction and edges opposed in the cross machine direction;
   c. disposing a fastener on the first side panel web, the fastener located between the waist edge and the leg opening edge;
   d. overlaying the first side panel web on the garment chassis web,
   e. attaching the first side panel web to the garment chassis web, whereby the side panel web remains substantially between the edges of the garment chassis web;
   f. providing a second side panel web with a waist edge and a leg opening edge and disposing a second fastener on the second side panel web; and attaching the side panel web to the garment chassis web, whereby the second side panel web remains substantially between the edges of the garment chassis web; and
   g. through cutting or providing a line of weakness on the first and second side panel webs.

2. The method of making a refastenable garment with attached side panels and a longitudinal axis in the cross machine direction according to claim 1, further comprising:
   through cutting or providing a line of weakness on the first side panel web and the first fastener.

3. The method of making a refastenable garment with attached side panels and a longitudinal axis in the cross machine direction according to claim 1, further comprising:
   through cutting or providing a line of weakness on the second fastener.

4. The method of making a refastenable garment with attached side panels and a longitudinal axis in the cross machine direction according to claim 1, further comprising:
   through cutting or providing a line of weakness on the first and second fasteners.

5. The method of making a refastenable garment with attached side panels and a longitudinal axis in the cross machine direction according to claim 1, further comprising:
   aligning the first side panel web waist edge to a first edge of the garment chassis web, and securing the first side panel web to the garment chassis web with bonds extending in the cross machine direction.

6. The method of making a refastenable garment with attached side panels and a longitudinal axis in the cross machine direction according to claim 1, further comprising:
   aligning the second side panel web waist edge to a second edge of the garment chassis web, and securing the second side panel web to the garment chassis web with bonds extending in the cross machine direction.

7. The method of making a refastenable garment with attached side panels and a longitudinal axis in the cross machine direction according to claim 1, further comprising:
   aligning the first side panel web waist edge to a first edge of the garment chassis web, and securing the first side panel web to the garment chassis web with bonds extending in the cross machine direction; and
   aligning the second side panel web waist edge to a second edge of the garment chassis web, and securing the second side panel web to the garment chassis web with bonds extending in the cross machine direction.

8. The method of making a refastenable garment with attached side panels and a longitudinal axis in the cross machine direction according to claim 1, further comprising:
   providing at least one of the first and second fasteners as a hinged fastener element.

9. The method of making a refastenable garment with attached side panels and a longitudinal axis in the cross machine direction according to claim 1 further comprising:
   providing the garment chassis web with an absorbent structure.

10. The method of making a refastenable garment with attached side panels and a longitudinal axis in the cross machine direction according to claim 1 further comprising:
    individuating the garment by separating the garment chassis web with the first side panel web and first fastener thereon with a cut across the garment chassis web in the cross machine direction.

11. A method of making a refastenable garment with attached side panels and a longitudinal axis in the cross machine direction comprising:
    a. providing a first side panel web with a waist edge and a leg opening edge;
    b. providing a garment chassis web with a longitudinal axis in the machine direction and edges opposed in the cross machine direction;
    c. disposing a fastener on the first side panel web, the fastener located between the waist edge and the leg opening edge;
    d. overlaying the first side panel web on the garment chassis web,
    e. attaching the first side panel web to the garment chassis web, whereby the side panel web remains substantially between the edges of the garment chassis web;
    f. providing a second side panel web with a waist edge and a leg opening edge and disposing a second fastener on the second side panel web; and attaching the side panel web to the garment chassis web, whereby the second side panel web remains substantially between the edges of the garment chassis web; and
    g. placing at least a portion of the first fastener and the second fastener in fastening contact by a single fold to the garment chassis web.

12. The method of making a refastenable garment with attached side panels and a longitudinal axis in the cross machine direction according to claim 1 wherein:
    the first fastener is one of a loop material or a hook material.

13. The method of making a refastenable garment with attached side panels and a longitudinal axis in the cross machine direction according to claim 1 wherein:
    the first side panel web is made from material having stretch in a transverse direction of the garment.

14. The method of making a refastenable garment with attached side panels and a longitudinal axis in the cross machine direction according to claim 1 wherein:
    at least one of the first and second side panel webs is made from material having stretch in a transverse direction of the garment.

15. A method of making a refastenable absorbent garment with attached side panels and a longitudinal axis in the cross machine direction, comprising:
    a. providing an absorbent garment chassis web with a longitudinal axis in the machine direction and edges opposed in the cross machine direction;
    b. providing a first side panel web with a waist edge and a leg end edge, and securing a first fastener strip to the first side panel web, the first fastener strip disposed between the waist edge and the leg end edge and secured to the first side panel web at a preselected bonding width on either side of a longitudinal axis of the first fastener strip;
    c. providing a line of weakness in the first side panel web and the first fastener strip at the longitudinal axis of the first fastener strip;
    d. aligning the waist edge of the first side panel web to a first edge of the absorbent chassis web with the leg end edge proximal to the longitudinal axis of the absorbent chassis web and bonding the first side panel web with the first fastener strip thereon to the absorbent chassis web with bonds extending in the cross machine direction;
    e. providing a second side panel web with a waist edge and a leg end edge and disposing a second fastener member on the second side panel web, the second fastener member disposed between the waist edge and the leg end edge of the second side panel web;
    f. providing a line of weakness in the second side panel web and the second fastener member at a longitudinal axis of the second fastener member;
    g. aligning the second side panel web waist edge to a second edge of the absorbent chassis web with the second side panel web leg end edge proximal to the longitudinal axis of the absorbent chassis web, and with the first fastener strip and the second fastener member aligned in opposition, and bonding the second side panel web with the second fastener member thereon to the absorbent chassis web with bonds extending in the cross machine direction;
    h. individuating an absorbent garment by separating the absorbent chassis web, with the first and second side panel webs and the first fastener strip and the second fastener member thereon, with a cut across the absorbent chassis web in the cross machine direction; and
    i. folding the absorbent chassis web or individuated garment to place the first fastener strip and the second fastener member in fastening contact.

16. The method of making a refastenable absorbent garment with attached side panels and a longitudinal axis in the cross machine direction, according to claim 15 wherein the securing of the first fastener strip to the first side panel web, and the side panel webs to the absorbent chassis web, is done by ultrasonic bonding and adhesive reinforcement.

17. The method of making a refastenable garment with attached side panels and a longitudinal axis in the cross machine direction according to claim 15 wherein at least one of the first and second side panel webs is made from spunbond laminate.

18. The method of making a refastenable garment with attached side panels and a longitudinal axis in the cross machine direction according to claim 15 wherein at least one of the first and second side panel webs is made from material having stretch in the transverse direction of the garment.

* * * * *